US012208210B2

(12) United States Patent
Grashow et al.

(10) Patent No.: US 12,208,210 B2
(45) Date of Patent: Jan. 28, 2025

(54) WRAP-BACK HEADGEAR FOR PATIENT INTERFACE

(71) Applicant: KONINKLIJKE PHILIPS N.V., Eindhoven (NL)

(72) Inventors: Jonathan Sayer Grashow, Monroeville, PA (US); Robert Edward O'Grady, Pittsburgh, PA (US); Dina Colangelo, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 577 days.

(21) Appl. No.: 17/484,326

(22) Filed: Sep. 24, 2021

(65) Prior Publication Data

US 2022/0096770 A1 Mar. 31, 2022

Related U.S. Application Data

(60) Provisional application No. 63/085,233, filed on Sep. 30, 2020.

(51) Int. Cl.
*A61M 16/06* (2006.01)
(52) U.S. Cl.
CPC .... *A61M 16/0627* (2014.02); *A61M 16/0605* (2014.02); *A61M 16/0633* (2014.02); *A61M 16/0666* (2013.01); *A61M 16/0683* (2013.01); *A61M 2205/0216* (2013.01)

(58) Field of Classification Search
CPC .. A61M 16/06–0694; A62B 9/00; A62B 9/04; A62B 18/00; A62B 18/02–08; A62B 18/084
See application file for complete search history.

(56) References Cited

U.S. PATENT DOCUMENTS

| 6,422,238 B1* | 7/2002 | Lithgow | A61M 16/0683 |
| | | | 128/206.13 |
| 7,779,832 B1 | 8/2010 | Ho | |
| 2014/0083429 A1 | 3/2014 | Rothermel | |
| 2016/0325067 A1* | 11/2016 | Harwood | A61M 16/0816 |
| 2019/0001095 A1 | 1/2019 | Rose | |
| 2019/0091429 A1 | 3/2019 | Oldenburg | |
| 2019/0175863 A1* | 6/2019 | Hocking | A61M 16/0616 |
| 2020/0129720 A1 | 4/2020 | Hammer | |
| 2020/0338294 A1* | 10/2020 | McLauren | A61M 16/0616 |

(Continued)

FOREIGN PATENT DOCUMENTS

| DE | 102008004252 A1 * | 7/2008 | ........ A61M 16/0633 |
| DE | 202005021927 U1 * | 7/2011 | ........ A61M 16/0057 |
| DE | 10254399 B4 * | 6/2017 | ............ A61M 16/06 |

OTHER PUBLICATIONS

Ising et al. Headband assembly for applying a breathing mask DE 10254399 B4 English translation (Year: 2017).*

(Continued)

*Primary Examiner* — Rachel T Sippel
(74) *Attorney, Agent, or Firm* — Michael W. Haas

(57) ABSTRACT

A headgear for use with a patient interface for providing a flow of pressurized breathing gas to the airway of a patient includes a pair of wrapping panels positioned at a rear thereof. The wrapping panels prevent the tension in the neck of a patient that commonly results when non-wrapping headgear is tightened.

14 Claims, 12 Drawing Sheets

(56) References Cited

U.S. PATENT DOCUMENTS

2021/0213231 A1 7/2021 Spear
2022/0323705 A1* 10/2022 Rummery ......... A61M 16/0666

OTHER PUBLICATIONS

Bechtel et al. DE 102008004252 A1 English translation (Year: 2008).*
ResMed De 202005021927 U1 English translation (Year: 2011).*
International Search Report for PCT/EP2021/075594 filed Sep. 17, 2021.

* cited by examiner

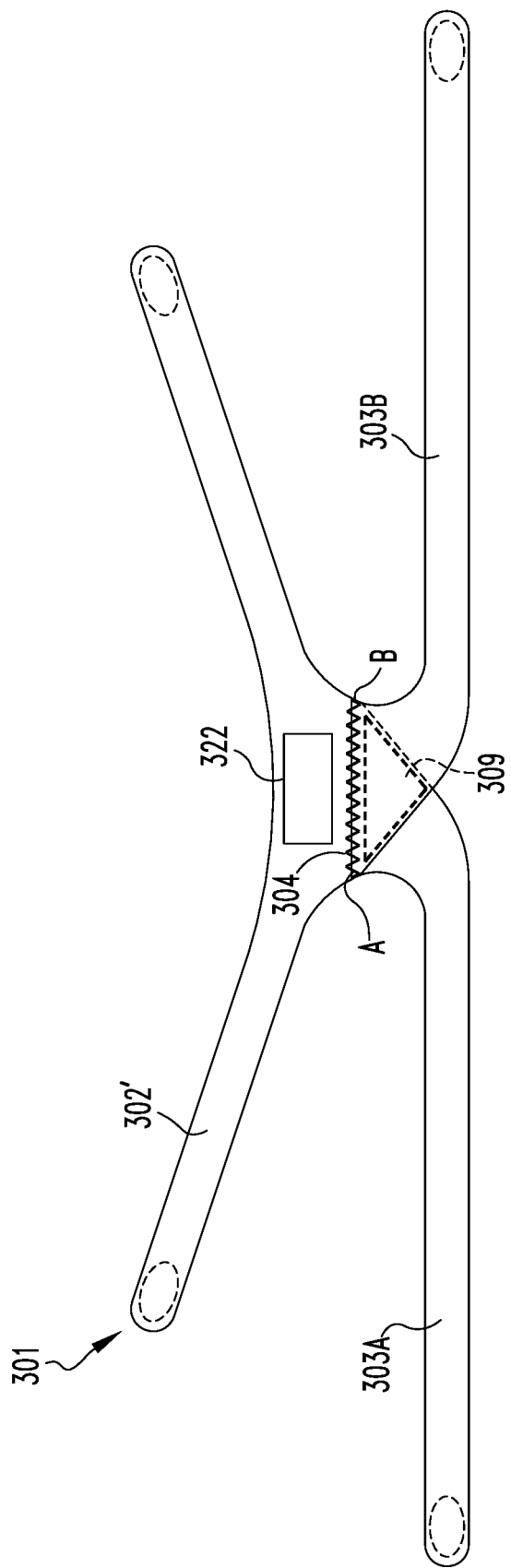

WRAP-BACK HEADGEAR FOR PATIENT INTERFACE

CROSS-REFERENCE TO RELATED APPLICATIONS

This patent application claims the priority benefit under 35 U.S.C. § 119(e) of U.S. Provisional Application No. 63/085,233, filed on Sep. 30, 2020, the contents of which are herein incorporated by reference.

BACKGROUND OF THE INVENTION

1. Field of the Invention

The disclosed concept pertains to headgear for use with a patient interface for supplying a pressurized flow of breathable gas to an airway of a patient. More particularly, the present invention pertains to headgear that reduce tension in the neck of a patient.

2. Description of the Related Art

Patient interfaces are used to deliver a flow of breathing gas to a user in a variety of contexts. Pressurized breathing gas in particular is often used to treat medical disorders. For example, it is known to deliver positive airway pressure (PAP) to treat conditions such as chronic obstructive pulmonary disease (COPD) or sleep apnea syndrome, in particular, obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle.

OSA is usually caused by an obstruction of the upper airway. It is characterized by repetitive pauses in breathing during sleep and is usually associated with a reduction in blood oxygen saturation. Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces a ventilator or pressure/flow generating device with the airway of the patient, so that a flow of breathing gas can be delivered from the ventilator or pressure/flow generating device to the airway of the patient. It is known to maintain such devices on the face of a wearer by a headgear having one or more straps adapted to fit over/around the patient's head. Because such patient interface devices are typically worn for an extended period of time, for example, overnight as a patient sleeps, it is important for the headgear to maintain the mask component of the device in a tight enough seal against the patient's face without discomfort.

With typical headgear designs, tightening the fit of the headgear in order to maintain the mask component in a tight seal against the patient's face often leads to discomfort and tension in the patient's neck. There is thus room for improvement in the design of headgear used to secure patient interfaces to the face of a patient.

SUMMARY OF THE INVENTION

Accordingly, it is an object of the present invention to provide, in one embodiment, a headgear for use with a patient interface for supplying a pressurized flow of breathable gas to an airway of a patient, wherein the headgear is configured to secure the patient interface to a face of the patient and comprises: a first wrapping panel configured to be disposed against a rear side of a head of the patient, the first wrapping panel having an upper portion structured to be coupled to the patient interface via at least one upper strap portion and a lower portion structured to be coupled to the patient interface via a first lower strap portion passing below an ear of the patient along a first side of the head of the patient when the patient interface is secured to the face of the patient via the headgear; and a second wrapping panel configured to be disposed against a rear side of the head of the patient, the second wrapping panel having an upper portion coupled to the upper portion of the first wrapping panel, the upper portion of the second wrapping panel being structured to be coupled to the patient interface via the at least one upper strap portion, and a lower portion structured to be coupled to the patient interface via a second lower strap portion passing below another ear of the patient along a second side of the head of the patient opposite the first side, wherein a portion of the second wrapping panel overlaps a corresponding portion of the first wrapping panel in an overlap region disposed between the upper and lower portions of each of the first wrapping panel and the second wrapping panel.

The upper portion of the first wrapping panel and the upper portion of the second wrapping panel may be coupled via a first seam disposed at a first edge of the overlap region and a second seam disposed at a second edge of the overlap region opposite the first edge and spaced a distance from the first seam. The first wrapping panel and the second wrapping panel may be coupled together solely at the upper portions thereof. The headgear may further comprise a stabilizing panel produced from an extensible material, the stabilizing panel being coupled to the lower portion of the first wrapping panel and the lower portion of the second wrapping panel.

In another embodiment, a headgear for use with a patient interface for supplying a pressurized flow of breathable gas to an airway of a patient is configured to secure the patient interface to a face of the patient and comprises: a horizontal panel configured to be disposed against a rear side of a head of the patient, the horizontal panel having a first strap portion structured to be coupled to the patient interface and passing along a first side of the head of the patient when the patient interface is secured to the face of the patient via the headgear and having a second strap portion structured to be coupled to the patient interface and passing along a second side of the head of the patient opposite the first side when the patient interface is secured to the face of the patient via the headgear; a first wrapping panel configured to be disposed against the rear side of the head of the patient, the first wrapping panel having an upper portion coupled to the horizontal panel and a lower portion structured to be coupled to the patient interface via a first lower strap portion passing below an ear of the patient along the first side of the head of the patient when the patient interface is secured to the face of the patient via the headgear; and a second wrapping panel configured to be disposed against the rear side of the head of the patient, the second wrapping panel having an upper portion coupled to the horizontal panel, the upper portion of the second wrapping panel being structured to be coupled to the patient interface and having a lower portion structured to be coupled to the patient interface via a second lower strap portion passing below an ear of the patient along the second side of the head of the patient when the patient interface is secured to the face of the patient via the headgear, and wherein a portion of the second wrapping panel overlaps a corresponding portion of the first wrapping panel in an overlap region disposed between the upper and lower portions of each of the first wrapping panel and the second wrapping panel.

The first wrapping panel and the second wrapping panel may be coupled together solely at the upper portions thereof. The headgear may further comprise a stabilizing panel produced from an extensible material, the stabilizing panel being coupled to the lower portion of the first wrapping panel and the lower portion of the second wrapping panel. A thickness of the portion of the first wrapping panel in the overlap region may be less than a thickness of portions of the first wrapping panel not in the overlap region and a thickness of the portion of the second wrapping panel in the overlap region may be less than a thickness of portions of the second wrapping panel not in the overlap region. The headgear may further comprise a number of venting portions, each of the number of venting portions comprising at least one of: a number of openings in the portion of the first wrapping panel in the overlap region, a number of openings in the portion of the second wrapping panel in the overlap region, and/or a number of openings in the horizontal panel.

In another embodiment, an arrangement for providing a flow of breathing gas to an airway of a patient comprises: a patient interface structured to be operatively coupled to a breathing gas generator via a delivery conduit; and a headgear, wherein the headgear is configured to secure the patient interface to a face of the patient and comprises: a first wrapping panel configured to be disposed against a rear side of a head of the patient, the first wrapping panel having an upper portion structured to be coupled to the patient interface and a lower portion structured to be coupled to the patient interface via a first lower strap portion passing below an ear of the patient along a first side of the head of the patient when the patient interface is secured to the face of the patient via the headgear; and a second wrapping panel configured to be disposed against the rear side of the head of the patient, the second wrapping panel having an upper portion coupled to the upper portion of the first wrapping panel, the upper portion of the second wrapping panel being structured to be coupled to the patient interface, and a lower portion structured to be coupled to the patient interface via a second lower strap portion passing below an ear of the patient along a second side of the head of the patient opposite the first side when the patient interface is secured to the face of the patient via the headgear, and wherein a portion of the second wrapping panel overlaps a corresponding portion of the first wrapping panel in an overlap region disposed between the upper and lower portions of each of the first wrapping panel and the second wrapping panel.

The upper portion of the first wrapping panel may be coupled to the patient interface via at least one first upper strap portion and the upper portion of the second wrapping panel may be coupled to the patient interface via at least one second upper strap portion. The arrangement may further comprise a manifold structured to be operatively coupled to the delivery conduit and a number of tubing members, each tubing member having a first end operatively coupled to the manifold and a second end operatively coupled to the patient interface. The at least one first upper strap portion of the first wrapping panel may be coupled to the patient interface via a first tubing member of the number of tubing members and the at least one second upper strap portion of the second wrapping panel may be coupled to the patient interface via a second tubing member of the number of tubing members.

The arrangement may further comprise a horizontal panel configured to be disposed against the rear side of the head of the patient, the horizontal panel having a first strap portion structured to be coupled to the patient interface and passing along the first side of the head of the patient when the patient interface is secured to the face of the patient via the headgear and a second strap portion structured to be coupled to the patient interface and passing along the second side of the head of the patient when the patient interface is secured to the face of the patient via the headgear, wherein the upper portion of the first wrapping panel is coupled to the horizontal panel and is structured to be coupled to the patient interface via the horizontal panel and the upper portion of the second wrapping panel is coupled to the horizontal panel and is structured to be coupled to the patient interface via the horizontal panel. The arrangement may further comprise a number of venting portions, wherein the number of venting portions comprises at least one of: a number of openings in the portion of the first wrapping panel in the overlap region, a number of openings in the portion of the second wrapping panel in the overlap region, and/or a number of openings in the horizontal panel.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 4D shows another variation of the headgear shown in FIG. 4B in accordance with an exemplary embodiment of the present invention;

DETAILED DESCRIPTION OF EXEMPLARY EMBODIMENTS

Figure 1A:
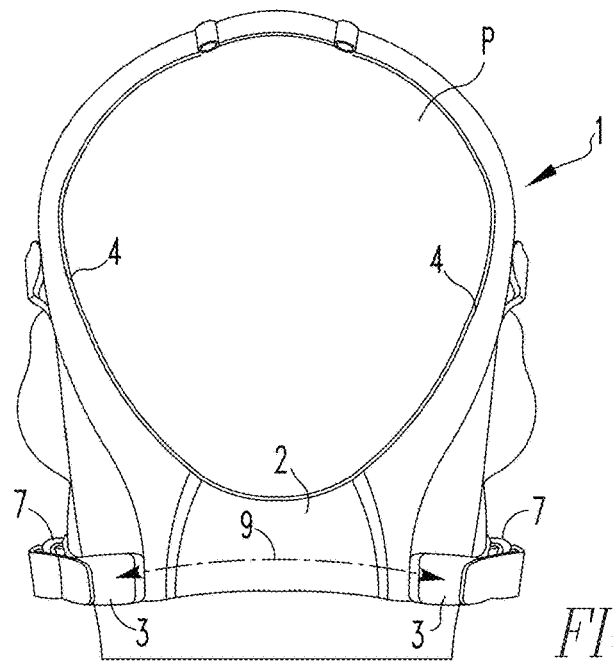
FIG. 1A is a rear view of a headgear representative of headgear known in the relevant field shown positioned on the head of a patient.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled in direct contact with each other. As used herein, "fixedly coupled" or "fixed" means that two components are coupled so as to move as one while maintaining a constant orientation relative to each other. As used herein, "movably coupled" means that two components are coupled so as to allow at least one of the components to move in a manner such that the orientation of the at least one component relative to the other component may change without the components being uncoupled.

As used herein, the statement that two or more parts or components are "integrated" shall mean that the parts or components are produced separately and subsequently joined together to produce a larger body. As used herein, the term "number" shall mean one or an integer greater than one (i.e., a plurality).

As used herein, the word "unitary" means a component is created as a single piece or unit. That is, a component that includes pieces that are created separately and then coupled together as a unit is not a "unitary" component or body. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1B:
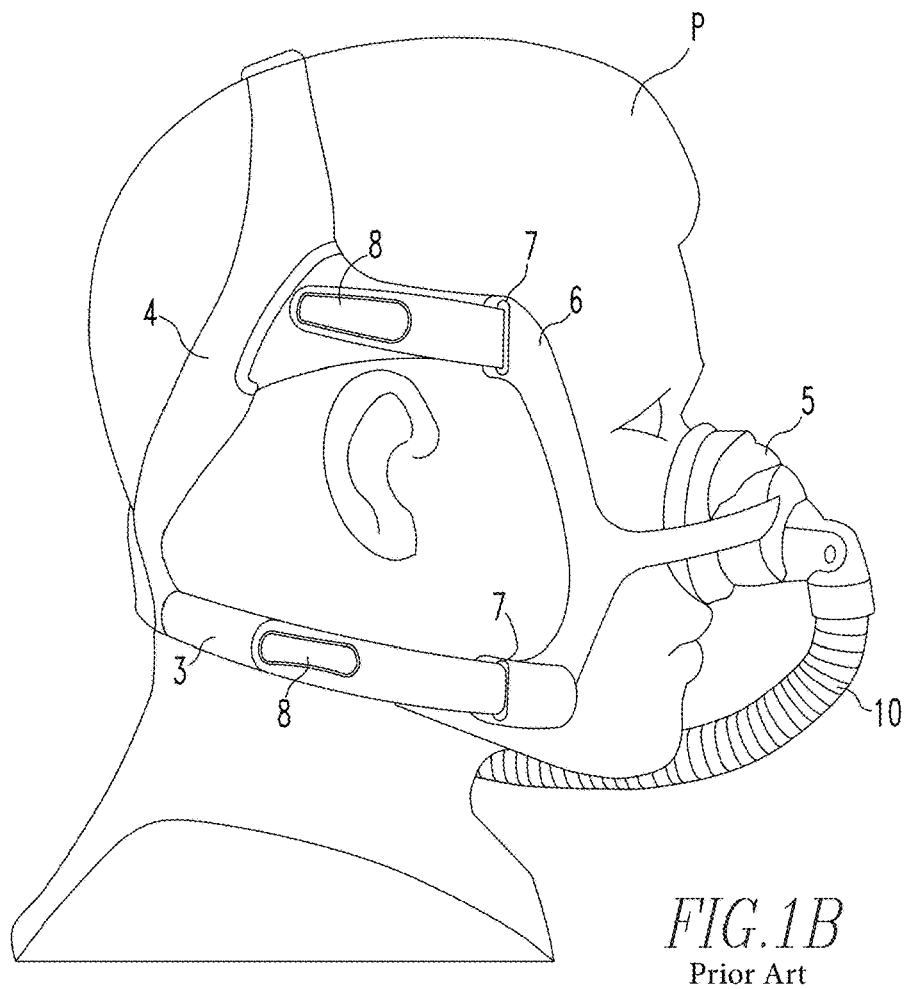
FIG. 1B is a side view of the headgear shown in FIG. 1A positioned on the head of the patient.

The disclosed concept, as described in greater detail herein in connection with various particular exemplary embodiments, pertains to improvements in headgear for use with patient interfaces for supplying a pressurized flow of breathable gas to an airway of a patient. FIG. 1A is a rear view of a headgear 1 representative of headgear known in the relevant field shown positioned on the head of a patient P. FIG. 1B is a side view of headgear 1 shown in FIG. 1A positioned on the head of patient P. A patient interface 5 for supplying a flow of breathable gas to the airway of patient P is coupled to a frame 6, and headgear 1 secures patient interface 5 to the face of patient P via frame 6. A pressurized flow of breathable gas generated by a respiratory therapy device (not shown), for example a CPAP machine, is delivered to the airway of patient P via a delivery conduit 10 operatively coupled to patient interface 5.

Headgear 1 includes a central panel 2 with horizontal straps 3 and diagonal straps 4. Central panel 2, horizontal straps 3, and diagonal straps 4 may be produced as discrete components that are fixedly coupled to one another, for example by sewing, or may be produced as a unitary body. Horizontal straps 3 and diagonal straps 4 are coupled to frame 6 at coupling points 7 of frame 6. A coupling point 7 may, for example, comprise a slot into which a horizontal strap 3 or a diagonal strap 4 can be fed such that horizontal strap 3 or diagonal strap 4 can be folded back onto itself and fastened (e.g., via hook and loop or other suitable fastener) at a fastening point 8. Preventing the flow of pressurized gas from leaking from the interface between patient interface 5 and a patient necessitates that horizontal straps 3 and diagonal straps 4 be sufficiently taut to create a tight seal between the face of patient P and patient interface 5. However, while creating a tight seal between patient interface 5 and the face of patient P is necessary to ensure the efficacy of the respiratory therapy, tightening horizontal straps 3 creates tension across the bottom edge of panel 2 in the direction indicated by arrows 9. This tension exerts a normal (i.e., inward) force on the neck that results in neck pain, compression of the blood vessels, and headaches for many patients.

Figure 2A:
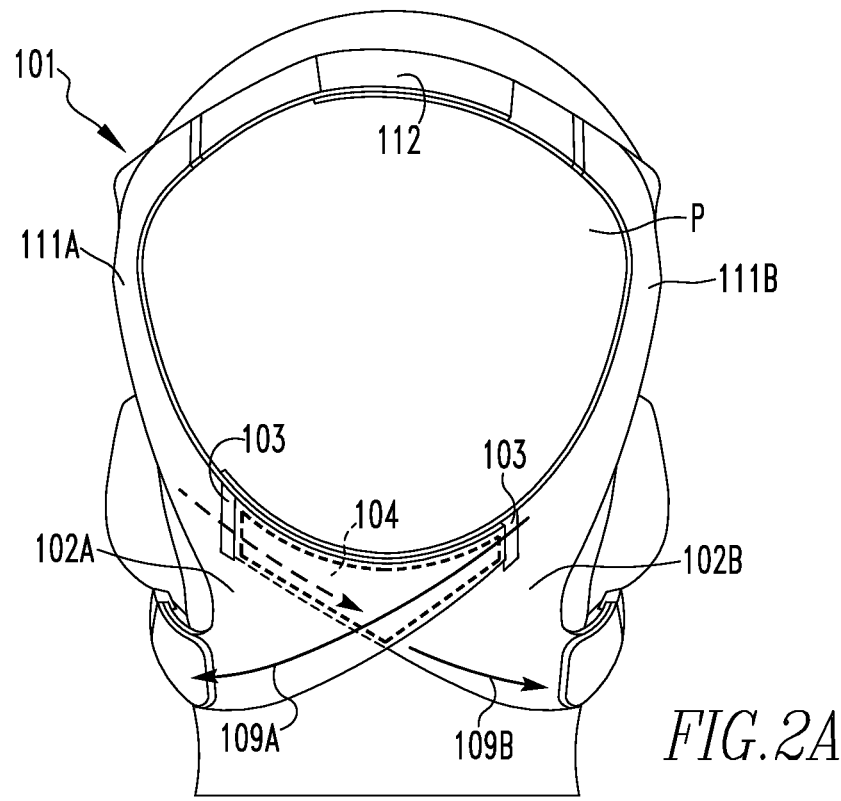
FIG. 2A is a rear view of a headgear in accordance with an exemplary embodiment of the present invention shown positioned on the head of a patient.
Figure 2B:
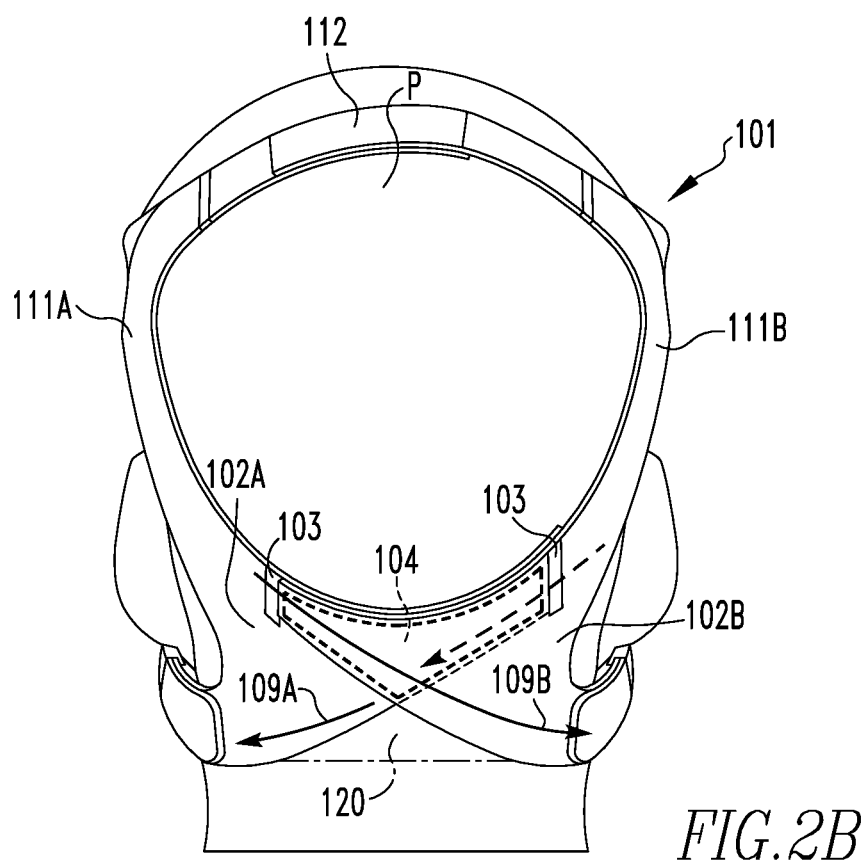
FIG. 2B is an alternative rear view of the headgear shown in FIG. 2A in accordance with an exemplary embodiment of the present invention shown positioned on the head of the patient.
Figure 2C:
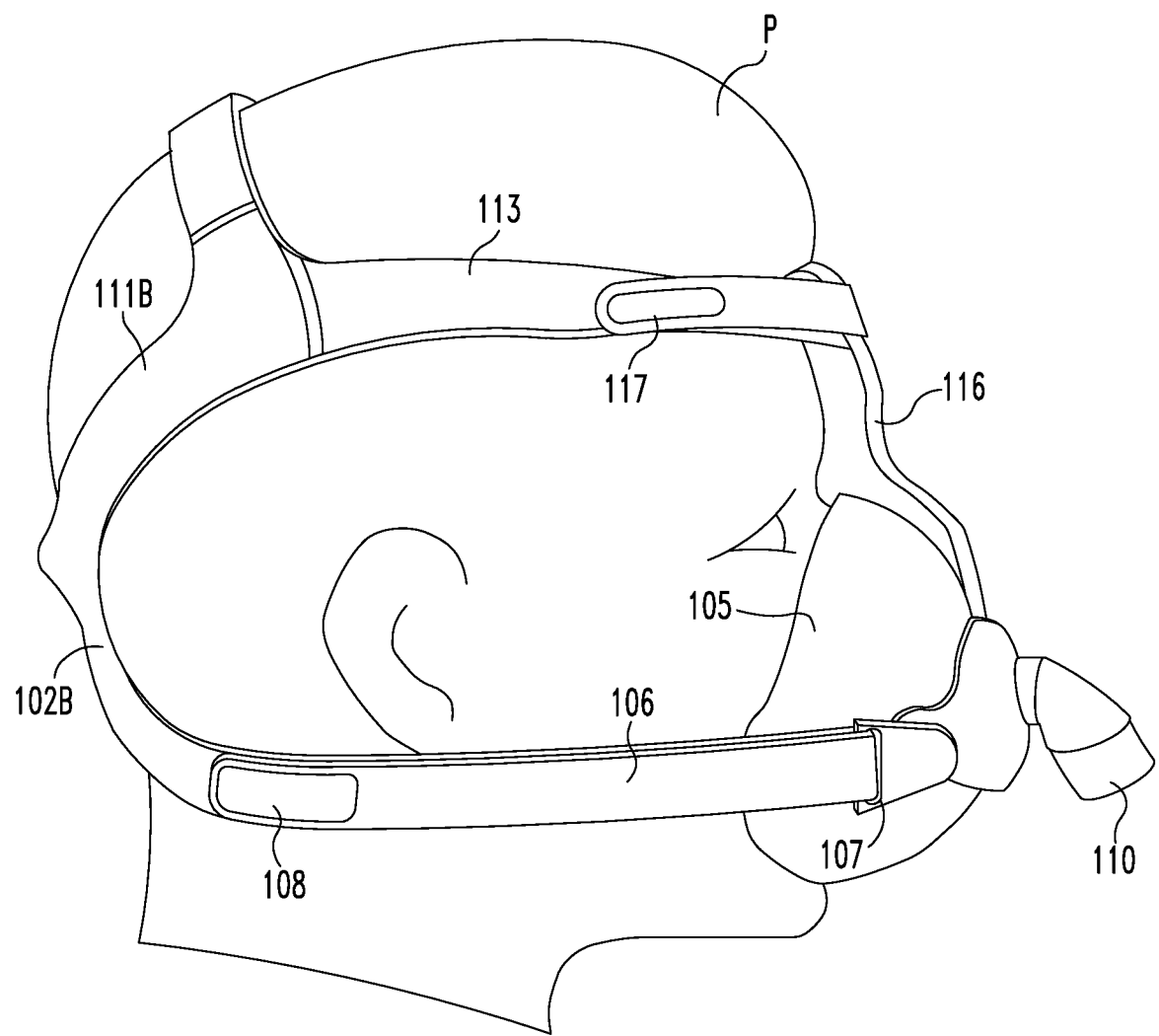
FIG. 2C is a side view of the headgear shown in FIG. 2A positioned on the head of the patient.

FIGS. 2A and 2B show alternative rear views and FIG. 2C shows a side view of a headgear 101 in accordance with a non-limiting exemplary embodiment of the disclosed concept positioned on the head of patient P. Headgear 101 and all other exemplary embodiments of the present invention can be produced from fabric, neoprene, or other suitable material. Headgear 101 secures a patient interface 105 to the face of patient P via strap portions 106, 113 and a forehead support frame 116 coupled to patient interface 105. A pressurized flow of breathable gas generated by a respiratory therapy device (not shown) is delivered to the airway of patient P via a delivery conduit 110 operatively coupled to patient interface 105.

Headgear 101 alleviates the normal force that headgear known in the relevant field (such as headgear 1 of FIGS. 1A and 1B) exert on the neck of a patient, and thus represents an improvement to such headgear known in the relevant field. Headgear 101 comprises two wrapping panels 102A, 102B (collectively, wrapping panels 102) that are coupled to one another solely at upper portions of each panel 102A, 102B via vertical seams 103 and partially overlap one another in an overlap region 104 as generally shown in dashed line in FIGS. 2A and 2B. Each wrapping panel 102 includes a lower portion from which a lower strap portion 106 extends and an upper portion from which an upper strap portion 113 extends, with overlap region 104 being disposed between said lower portion and said upper portion of each wrapping panel 102. Both wrapping panels 102 are reflectively identical to one another and either wrapping panel 102 can be disposed on top (i.e., opposite the patient facing side) of the other wrapping panel 102 in overlap region 104. For example, FIG. 2A shows wrapping panel 102A disposed on top of wrapping panel 102B in overlap region 104 and FIG. 2B shows an alternative arrangement wherein wrapping panel 102B is disposed on top of wrapping panel 102A in overlap region 104.

Each lower strap portion 106 is configured to pass below an ear of the patient along a side of the head of the patient and is structured to be coupled to patient interface 105. In one non-limiting example, patient interface 105 comprises a coupling point 107 for each lower strap portion 106, and each coupling point 107 comprises a slot into which a lower strap portion 106 can be passed through and then folded back onto itself and fastened (e.g., via hook and loop or other suitable fastener) at a fastening point 108, while each upper strap portion 113 is coupled to coupling point 117 and comprises either the hook portion or loop portion of a hook and loop fastener while coupling point 117 comprises the other of the hook portion or loop portion of the hook and loop fastener. It will be appreciated that any method suitable for coupling wrapping panels 102 to coupling points 107, 117 or to any other suitable arrangements of patient interface 5 may be used without departing from the scope of the disclosed concept. Additionally, it is to be appreciated that lower strap portions 106 may be formed as integral portions of wrapping panels 102 without varying from the scope of the disclosed concept.

Integrating wrapping panels 102 with one another via vertical seams 103 allows wrapping panels 102 to move relative to one another with more than one degree of freedom when either wrapping panel 102 is pulled in a direction indicated by arrows 109A, 109B (collectively, arrows 109). Specifically, when a wrapping panel 102 is pulled in the direction of an arrow 109 in order to tighten the seal between patient interface 105 and the face of patient P, the wrapping panel 102 simultaneously moves in both the horizontal and vertical directions relative to the viewing plane of FIGS. 2A and 2B. Variations of, or non-sewed substitutes for, vertical seams 103 may be used to couple wrapping panels 102 to one another while still allowing wrapping panels 102 to move relative to one another with more than one degree of freedom, without departing from the scope of the disclosed concept. For example and without limitation, other quantities, orientations and/or arrangements of seams may be used, and the location of the seams may be moved from the locations shown in FIGS. 2A and 2B without varying from the scope of the disclosed concept. When wrapping panels 102 are pulled in the directions indicated by arrows 109 to tighten the seal between patient interface 105 and the face of patient P, the wrap-back design of headgear 101 distributes any tension created in the wrapping panels 102 over a greater surface area than the horizontal straps 3 of headgear 1 of FIGS. 1A and 1B and significantly reduces the normal force felt by patient P on his or her neck as compared to the normal force felt when wearing headgear such as headgear 1.

In addition, integrating wrapping panels 102 via vertical seams 103 enables a diagonal strap portion 111A, 111B, of each wrapping panel 102A, 102B, respectively (collectively, diagonal strap portions 111) to maintain a fixed geometry even as wrapping panels 102 are pulled in the directions of arrows 109. Diagonal strap portions 111 may be integrated with one another at an upper region 112 of headgear 101, for example and without limitation using seams, or may be constructed to be coupled to one another in an adjustable manner, for example, without limitation using a hook and loop fastener or other suitable arrangement.

Referring to FIG. 2B, there may be a context in which it is desirable to modify the degrees of freedom with which wrapping panels 102 can move relative to one another when either wrapping panel 102 is pulled in a direction indicated by arrows 109. As such, in a further non-limiting exemplary embodiment, wrapping panels 102 can additionally be indirectly coupled to one another via an optional stabilizing panel 120 produced from material of lesser stiffness than the material from which wrapping panels 102 are produced, with the lower portion of each wrapping panel 102 being coupled to stabilizing panel 120 via a seam or other suitable arrangement. In such an embodiment, stabilizing panel 120 is produced from a highly extensible material or materials, for example and without limitation, elastane or knit elastic, such that headgear 101 still alleviates the normal force that headgear known in the relevant field (such as headgear 1 of FIGS. 1A and 1B) exert on the neck of a patient. It will be appreciated that the bottom edge (with respect to the view shown in FIG. 2B) of stabilizing panel 120 is depicted in phantom line in order to denote that stabilizing panel 120 can either be included in, or omitted from, headgear 101 without departing from the scope of the disclosed concept.

Figure 3A:
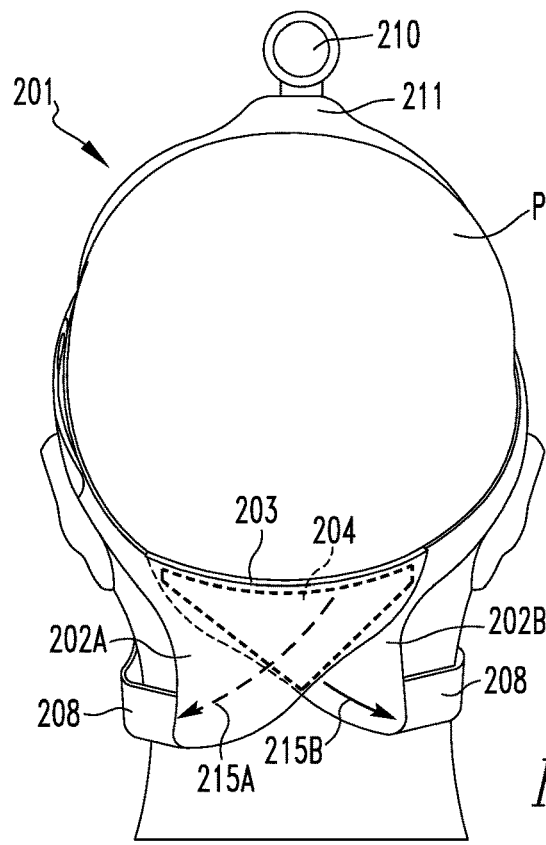
FIG. 3A is a rear view of a headgear in accordance with another exemplary embodiment of the present invention shown positioned on the head of a patient.
Figure 3B:
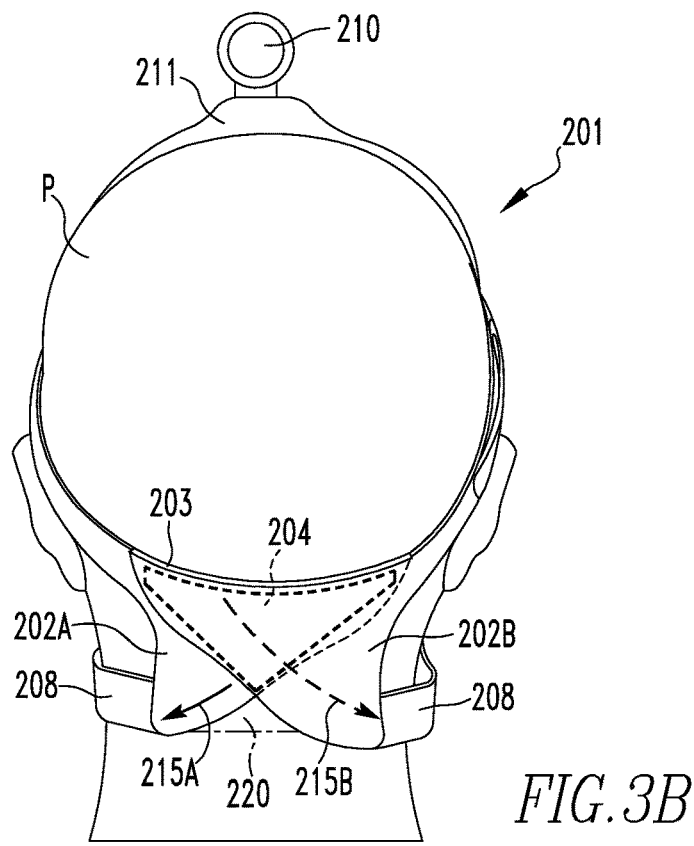
FIG. 3B is an alternative rear view of the headgear shown in FIG. 3A in accordance with an exemplary embodiment of the present invention shown positioned on the head of the patient.
Figure 3C:
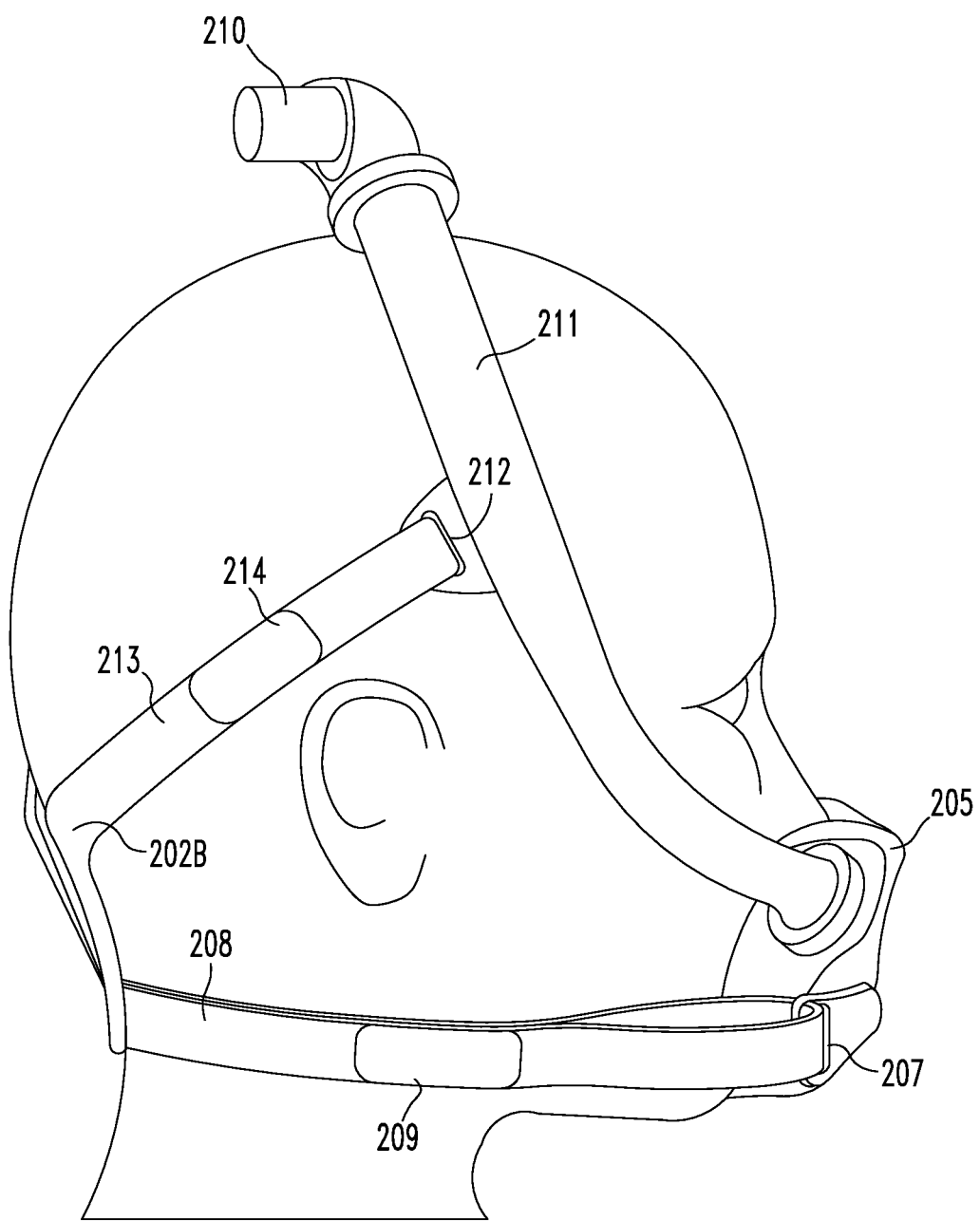
FIG. 3C is a side view of the headgear shown in FIG. 3A positioned on the head of the patient.

FIGS. 3A and 3B show alternative rear views and FIG. 3C shows a side view of a headgear 201 in accordance with another non-limiting exemplary embodiment of the disclosed concept positioned on the head of patient P. Similar to headgear 101, headgear 201 alleviates the normal force that headgear known in the relevant field (such as headgear 1 of FIGS. 1A and 1B) exerts on the neck of a patient, and represents another improvement to such headgear known in the relevant field. Headgear 201 secures a patient interface 205 to the face of patient P. A pressurized flow of breathable gas generated by a respiratory therapy device (not shown) can be delivered to the airway of patient P via a delivery conduit (not shown) that can be operatively coupled to a manifold 210, which in turn is operatively coupled to a first end of a number of tubing members 211, each of the number of tubing members 211 also having a second end operatively coupled to patient interface 205.

Headgear 201 comprises two wrapping panels 202A, 202B (collectively, wrapping panels 202) that are coupled to one another at horizontal seam 203 and partially overlap one another in an overlap region 204 such as generally shown in dashed line in FIGS. 3A and 3B. Each wrapping panel 202 includes a lower portion from which a lower strap portion 208 extends and an upper portion from which an upper strap portion 213 extends, with overlap region 204 being disposed between said lower portion and said upper portion of each wrapping panel 202. Both wrapping panels 202 are reflectively identical to one another and either wrapping panel 202 can be disposed on top (i.e., opposite the patient facing side) of the other wrapping panel 202 in overlap region 204. For example, FIG. 3A shows wrapping panel 202A disposed on top of wrapping panel 202B in overlap region 204, and FIG. 3B shows wrapping panel 202B disposed on top of panel 202A in overlap region 204.

Headgear 201 secures patient interface 205 to the face of patient P via a coupling point 207 that is part of patient interface 205. Each lower strap portion 208 is configured to pass below an ear of the patient along a side of the head of the patient and is structured to be coupled to patient interface 205 via coupling point 207. In one non-limiting example, coupling point 207 comprises a slot into which a corresponding lower strap portion 208 can be fed such that the lower strap portion 208 can be folded onto itself and fastened (e.g., via hook and look or other suitable fastening arrangement) at a fastening point 209 to form a loop. The number of tubing members 211 comprise coupling points 212 each of which, in one non-limiting example, comprises a slot into which a corresponding upper strap portion 213 can be fed such that the upper strap portion 213 can be folded back onto itself and fastened (e.g., via hook and look or other suitable fastening arrangement) at a fastening point 214 to form a loop.

Coupling wrapping panels 202 to each other via horizontal seam 203 allows both wrapping panels 202 to move relative to one another with more than one degree of freedom when either wrapping panel 202 is pulled in a direction indicated by arrows 215A, 215B (collectively, arrows 215). Specifically, when a wrapping panel 202 is pulled in the direction of an arrow 215 in order to tighten the seal between patient interface 205 and the face of patient P, the wrapping panel 202 simultaneously moves in both the horizontal and vertical directions relative to the viewing plane of FIGS. 3A and 3B. Variations on, or non-sewed substitutes for horizontal seam 203 may be used to couple wrapping panels 202 to one another while still allowing wrapping panels 202 to move relative to one another with more than one degree of freedom, without departing from the scope of the disclosed concept. When wrapping panels 202 are pulled in the directions indicated by arrows 215 to tighten the seal between patient interface 205 and the face of patient P, the wrap-back design of headgear 201 distributes any tension created in the wrapping panels 202 over a greater surface area than the horizontal straps 3 of headgear 1 and significantly reduces the normal force felt by patient P on his or her neck as compared to the normal force felt when wearing headgear such as headgear 1.

Referring to FIG. 3B, there may be a context in which it is desirable to modify the degrees of freedom with which wrapping panels 202 can move relative to one another when either wrapping panel 202 is pulled in a direction indicated by arrows 215. As such, in a further non-limiting exemplary embodiment, wrapping panels 202 can additionally be indirectly coupled to one other via an optional stabilizing panel 220 produced from material of lesser stiffness than the material from which wrapping panels 202 are produced, with the lower portion of each wrapping panel 202 being coupled to stabilizing panel 220 via a seam or other suitable arrangement. In such an embodiment, stabilizing panel 220 is produced from a highly extensible material or materials, for example and without limitation, elastane or knit elastic, such that headgear 201 still alleviates the normal force that headgear known in the relevant field (such as headgear 1 of FIGS. 1A and 1B) exert on the neck of a patient. It will be appreciated that the bottom edge (with respect to the view shown in FIG. 3B) of stabilizing panel 220 is depicted in phantom line in order to denote that stabilizing panel 220 can either be included in, or omitted from, headgear 201 without departing from the scope of the disclosed concept.

Figure 4A:
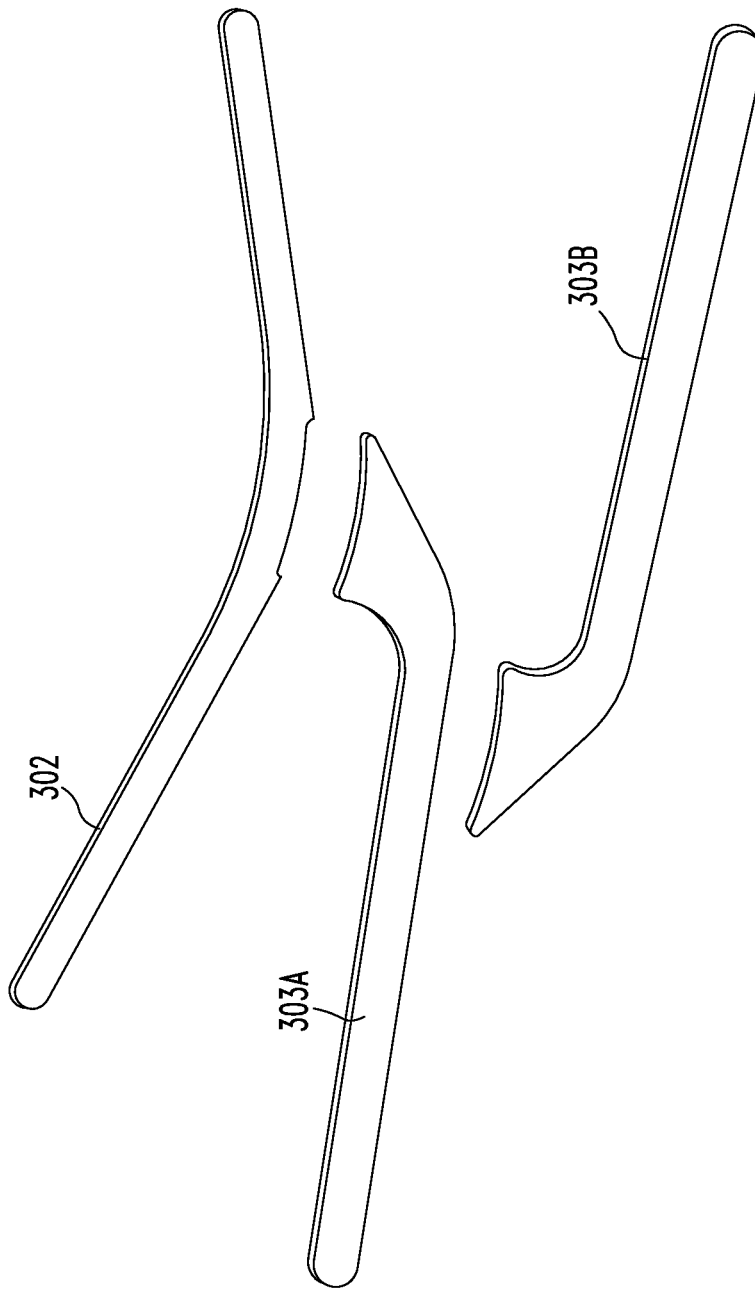
FIG. 4A shows separated components of a headgear in accordance with a further exemplary embodiment of the present invention.
Figure 4B:
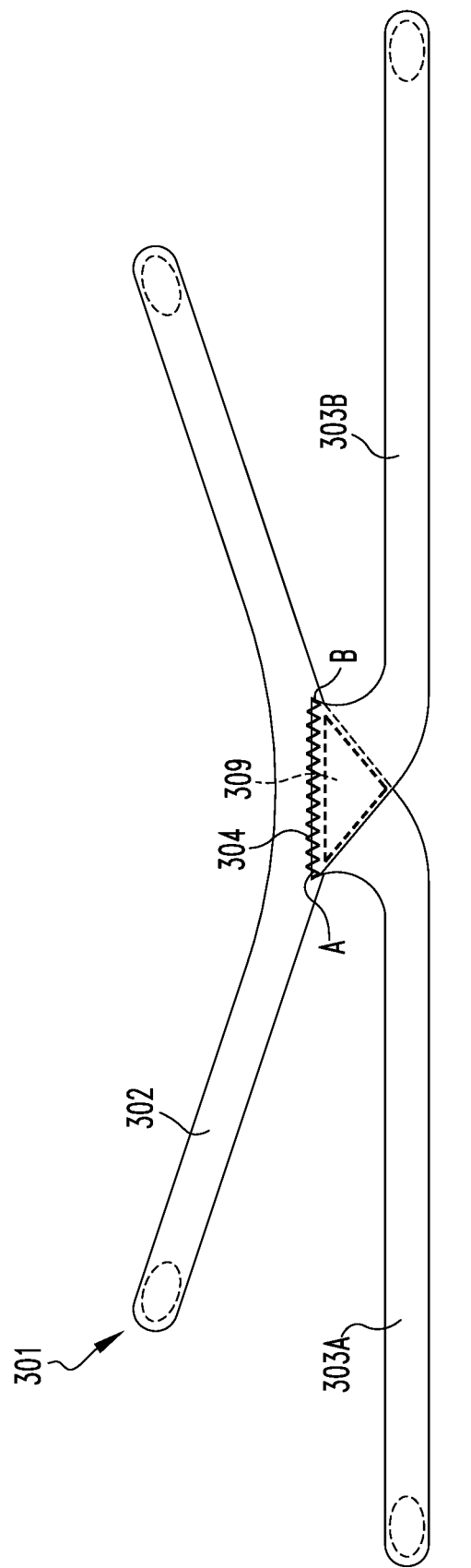
FIG. 4B shows the headgear formed after the components shown in FIG. 4A are integrated in accordance with an exemplary embodiment of the present invention.

FIG. 4A shows the separated components of a headgear 301, and FIG. 4B shows the components of FIG. 4A after being integrated to form headgear 301, in accordance with an additional non-limiting exemplary embodiment of the disclosed concept. Headgear 301 is a three-panel variation of the two-panel designs of headgear 101 and 201 and comprises a horizontal panel 302 in addition to two wrapping panels 303A, 303B (collectively, wrapping panels 303). FIG. 4B shows horizontal panel 302 and wrapping panels 303 integrated together at a central portion of horizontal panel 302 via a seam 304. While FIG. 4B depicts seam 304 spanning the entire distance between point A and point B, it will be appreciated that horizontal panel 302 and wrapping panels 303 can be integrated by means other than a seam spanning from point A to point B without departing from the scope of the disclosed concept. In one non-limiting example, localized stitching at point A and localized stitching at point B is used. While FIG. 4B depicts wrapping panel 303B disposed on top of (i.e., opposite the patient facing side) wrapping panel 303A in an overlap region 309, shown generally by dashed lines where the two wrapping panels 303 overlap near seam 304, it will be appreciated that wrapping panel 303A can alternatively be disposed on top of wrapping panel 303B in overlap region 309 without departing from the scope of the disclosed concept. Furthermore, while horizontal panel 302 and both wrapping panels 303 are shown in FIGS. 4A and 4B as being produced separately and subsequently integrated, it will be appreciated that horizontal panel 302 and a first of the wrapping panels 303 can be produced as a unitary body from a single sheet of material such that only the second of the wrapping panels 303 would need to be attached via seam 304 to the unitary body without departing from the scope of the disclosed concept.

Figure 4C:
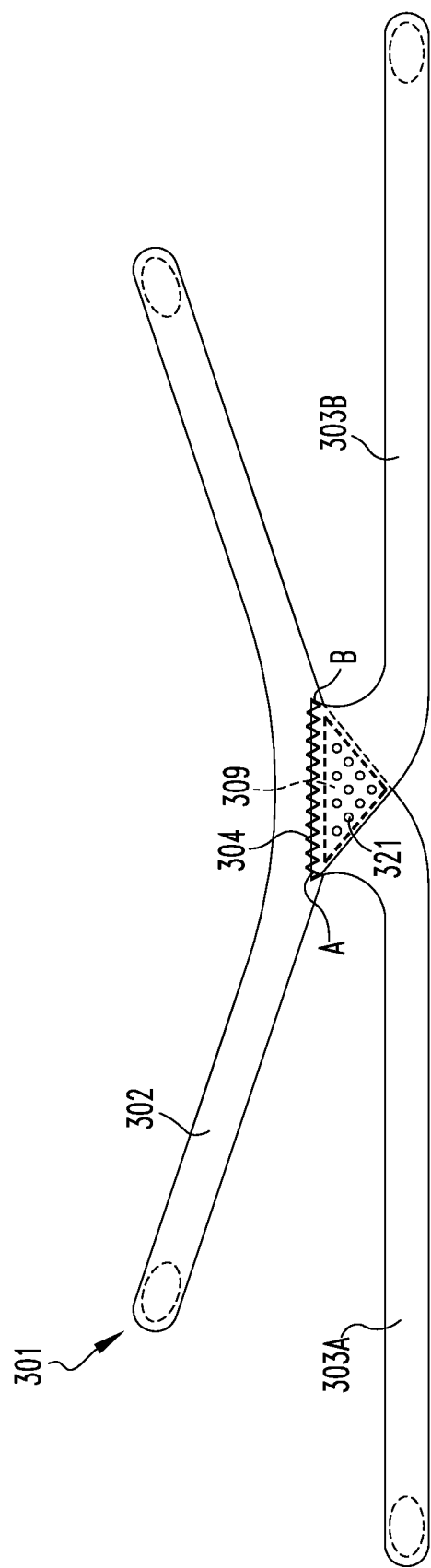
FIG. 4C shows a variation of the headgear shown in FIG. 4B in accordance with an exemplary embodiment of the present invention.

There may be a desire for increased airflow to the rear side of the head of patient P when both wrapping panels 303 are stacked at overlap region 309, and headgear 301 can be produced with various venting portions to increase air flow to the head of patient P. Referring to FIG. 4C, in one non-limiting exemplary embodiment, overlap region 309 of each wrapping panel 303 can be produced with a number of perforations 321. Referring to FIG. 4D, in another non-limiting exemplary embodiment, a horizontal panel 302' includes a vent 322 created by creating an opening in horizontal panel 302'. Whereas horizontal panel 302 is of substantially uniform width, the central portion of horizontal panel 302' near seam 304 is somewhat wider (taller in the view shown in FIG. 4D) in order to accommodate vent 322.

Figure 5A:
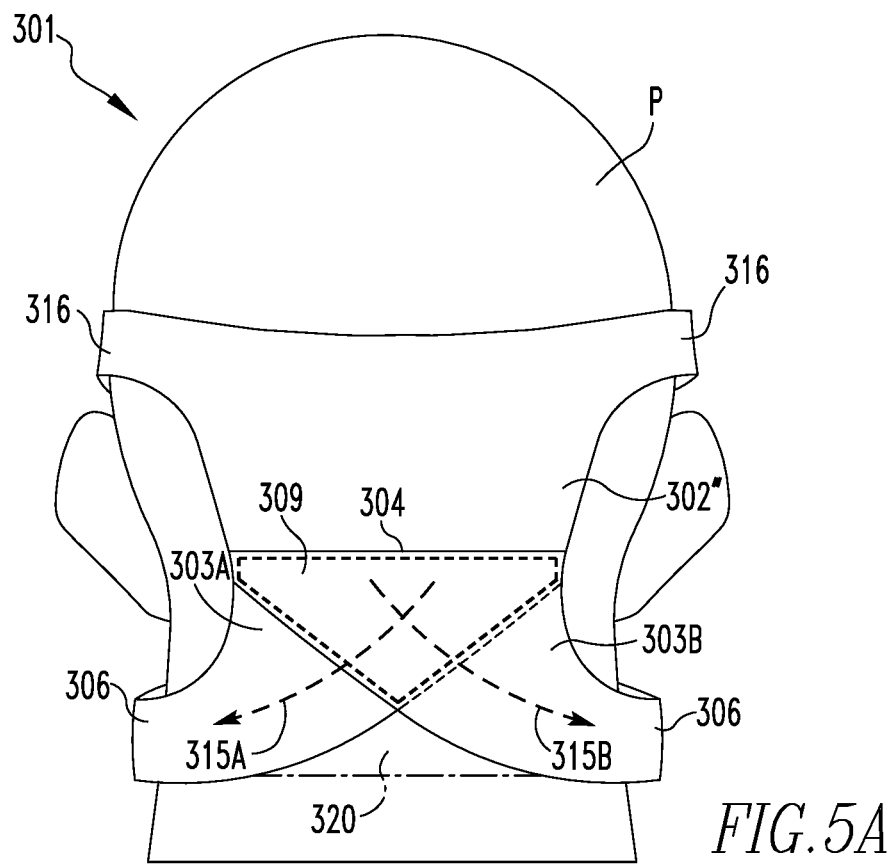
FIG. 5A is a rear view of a headgear that is an alternative exemplary embodiment of the headgear shown in FIG. 4B in accordance with yet another exemplary embodiment of the present invention shown positioned on the head of a patient in accordance with yet another exemplary embodiment of the present invention.
Figure 5B:
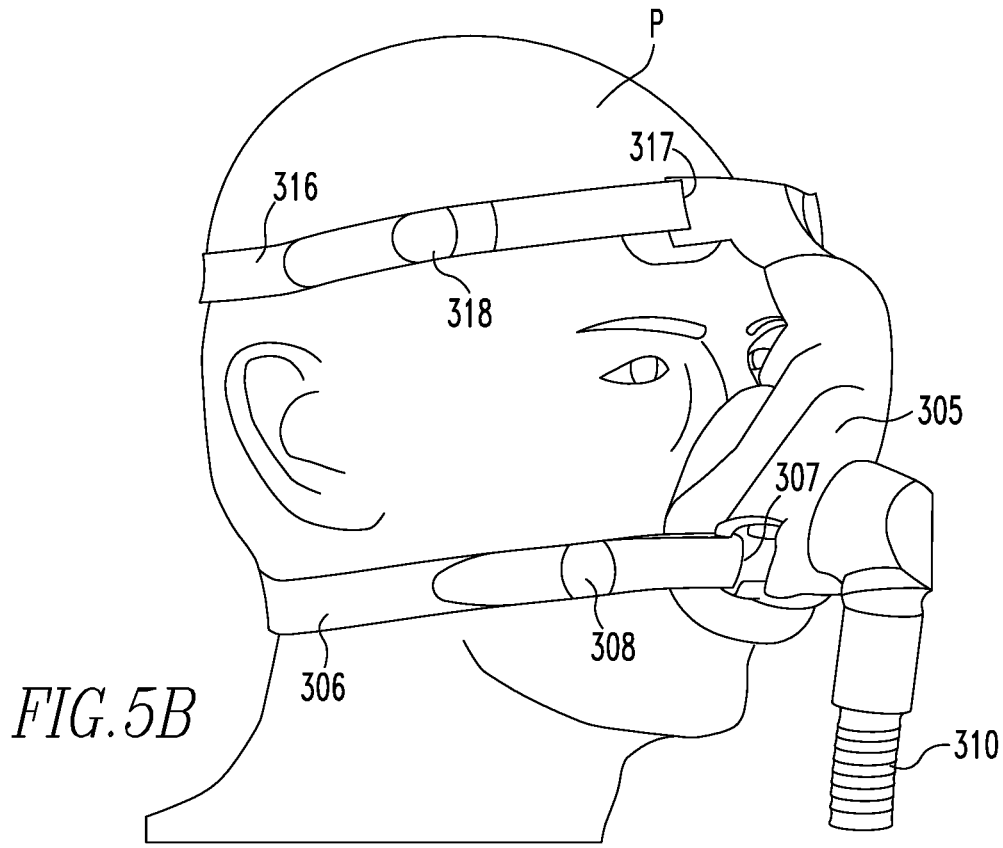
FIG. 5B is a side view of the headgear shown in FIG. 5A positioned on the head of the patient.

FIG. 5A is a rear view and FIG. 5B is a side view of an iteration of headgear 301, in accordance with a further non-limiting exemplary embodiment of the disclosed concept, positioned on the head of patient P. Headgear 301 shown in FIG. 5A comprises a horizontal panel 302" and two wrapping panels 303. Whereas horizontal panel 302 is of substantially uniform width, the central portion of horizontal panel 302" is noticeably wider (taller in the view shown in FIG. 5A) than the side regions. This wider iteration renders horizontal panel 302" better suited for coupling a patient interface with dimensions such as those of a patient interface 305 (shown in FIG. 5B) to the face of patient P. Headgear 301 secures patient interface 305 to the face of patient P via lower strap portions 306 of wrapping panels 303 and upper strap portions 316 of horizontal panel 302", each lower strap portion 306 extending from a lower portion of a wrapping panel 303 and being configured to pass below an ear of the patient along a side of the head of the patient, and each upper strap portion 316 extending from an upper portion of horizontal panel 302". Overlap region 309 is disposed between said lower portion of each wrapping panel 303 and an upper portion of each wrapping panel 303. Lower and upper strap portions 306, 316 can be coupled to patient interface 305 at coupling points 307, 317 of patient interface 305. In one non-limiting example, each coupling point 307, 317 comprises a slot into which a corresponding strap portion 306, 316 can be fed such that the strap portion 306, 316 can be folded onto itself and fastened at a fastening point 308, 318 to form a loop. A pressurized flow of breathable gas generated by a respiratory therapy device (not shown) can be delivered to the airway of patient P via a delivery conduit 310 operatively coupled to patient interface 305.

Coupling wrapping panels 303 to horizontal panel 302" (or horizontal panel 302) at an upper portion of each wrapping panel 303 allows both wrapping panels 303 to move relative to one another and relative to horizontal panel 302", 302 with more than one degree of freedom when either wrapping panel 303 is pulled in a direction indicated by arrows 315A, 315B (collectively, arrows 315). Specifically, when a wrapping panel 303 is pulled in the direction of an arrow 315 in order to tighten the seal between patient interface 305 and the face of patient P, the wrapping panel 303 simultaneously moves in both the horizontal and vertical directions relative to the viewing plane of FIG. 5B. Variations on or non-sewed substitutes for seam 304 may be used to couple wrapping panels 303 to one another and to the horizontal panel 302, 302" while still allowing wrapping panels 303 to move relative to one another and relative to horizontal panel 302, 302" with more than one degree of freedom, without departing from the scope of the disclosed concept. In one non-limiting example, seam 304 can be produced by welding rather than sewing. When wrapping panels 303 are pulled in the directions indicated by arrows 315 to tighten the seal between patient interface 205 and the face of patient P, the wrap-back design of headgear 301 distributes any tension created in the wrapping panels 303 over a greater surface area than the horizontal straps 3 of headgear 1 and significantly reduces the normal force felt by patient P on his or her neck as compared to the normal force felt when wearing headgear such as headgear 1.

Referring to FIG. 5A, there may be a context in which it is desirable to modify the degrees of freedom with which wrapping panels 303 can move relative to one another when either wrapping panel 303 is pulled in a direction indicated by arrows 315. As such, in a further non-limiting exemplary embodiment, wrapping panels 303 can additionally be indirectly coupled to one another via an optional stabilizing panel 320 produced from material of lesser stiffness than the material from which wrapping panels 303 are produced, with the lower portion of each wrapping panel 303 being coupled to stabilizing panel 320 via a seam or other suitable arrangement. In such an embodiment, stabilizing panel 320 is produced from a highly extensible material or materials, for example and without limitation, elastane or knit elastic, such that headgear 301 still alleviates the normal force that headgear known in the relevant field (such as headgear 1 of FIGS. 1A and 1B) exert on the neck of a patient. It will be appreciated that the bottom edge (with respect to the view shown in FIG. 5A) of stabilizing panel 320 is depicted in phantom line in order to denote that stabilizing panel 320 can either be included in, or omitted from, headgear 301 without departing from the scope of the disclosed concept.

Portions of headgear 301 may be varied in order to increase the comfort of a patient P while wearing headgear 301. In one non-limiting example, for each wrapping panel 302, the material in the overlap region 309 can be permanently compressed to be half as thick as the material in the regions outside of overlap region 309 so that when overlap regions 309 of both wrapping panels 302 are stacked together, the thickness of the two stacked overlap regions 309 is uniform in comparison with the other regions of each individual wrapping panel 309. This variation can be incorporated in headgear 101 and 201 as well, with overlap regions 104 and 204 of each wrapping panel 102 and 202 being permanently compressed to be half as thick as the material in the regions outside of overlap regions 104 and 204.

Figure 5C:
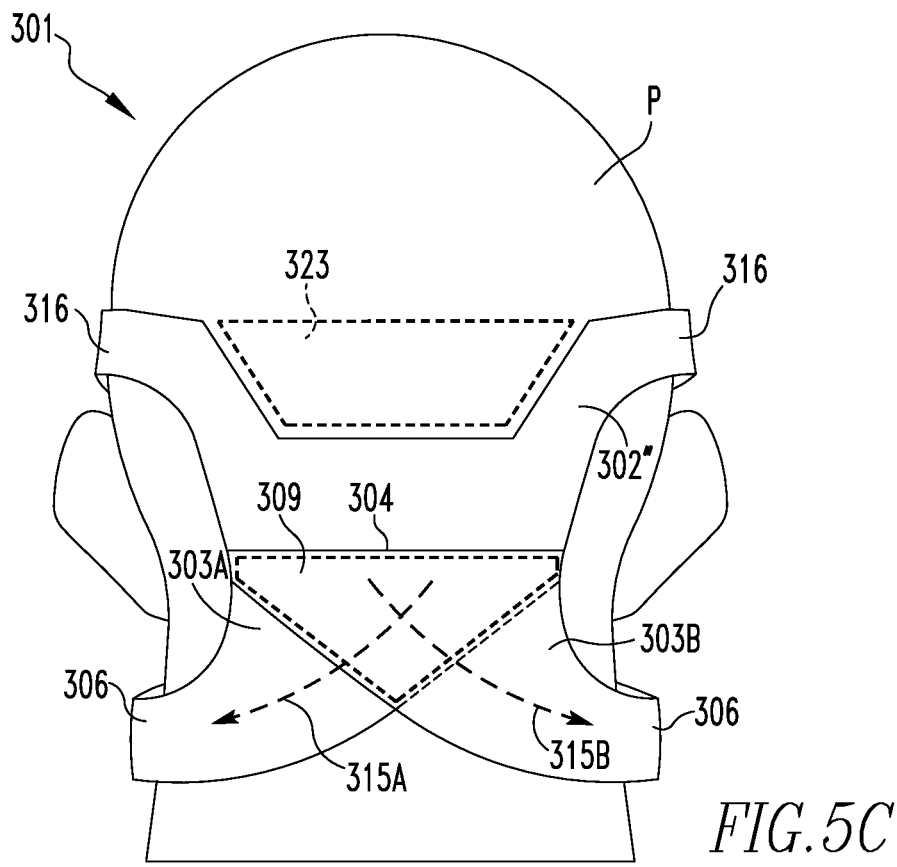
FIG. 5C shows a variation of the headgear shown in FIG. 5A in accordance with an exemplary embodiment of the present invention shown positioned on the head of a patient.

In addition, as stated previously with respect to FIGS. 4C and 4D, headgear 301 can include various venting portions to increase airflow to the head of patient P. In one non-limiting exemplary embodiment, referring to FIG. 5C, horizontal panel 302" can be produced by omitting or removing a region 323. In another non-limiting exemplary embodiment, referring to FIG. 5D, a wrapping panel 303A' can be produced by omitting material from the left side (with respect to the view shown in FIG. 5A) of wrapping panel 303A and by omitting material from the right side (with respect to the view shown in FIG. 5A) of wrapping panel 303B. Arrow 324A generally indicates how the left edge of wrapping panel 303A is moved closer toward a left edge of overlap region 309 to produce wrapping panel 303A', and arrow 324B generally indicates how the right edge of wrapping panel 303B is moved closer toward a right edge of overlap region 309 to produce wrapping panel 303B'.

Figure 5D:
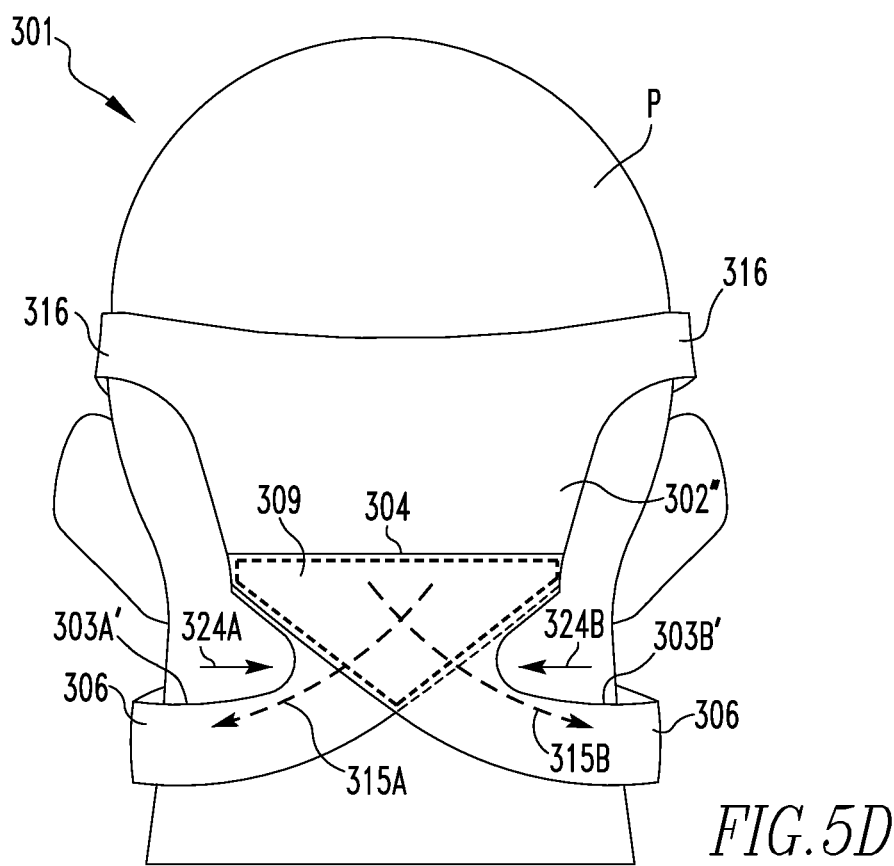
FIG. 5D shows another variation of the headgear shown in FIG. 5A in accordance with an exemplary embodiment of the present invention shown positioned on the head of a patient.
Figure 5E:
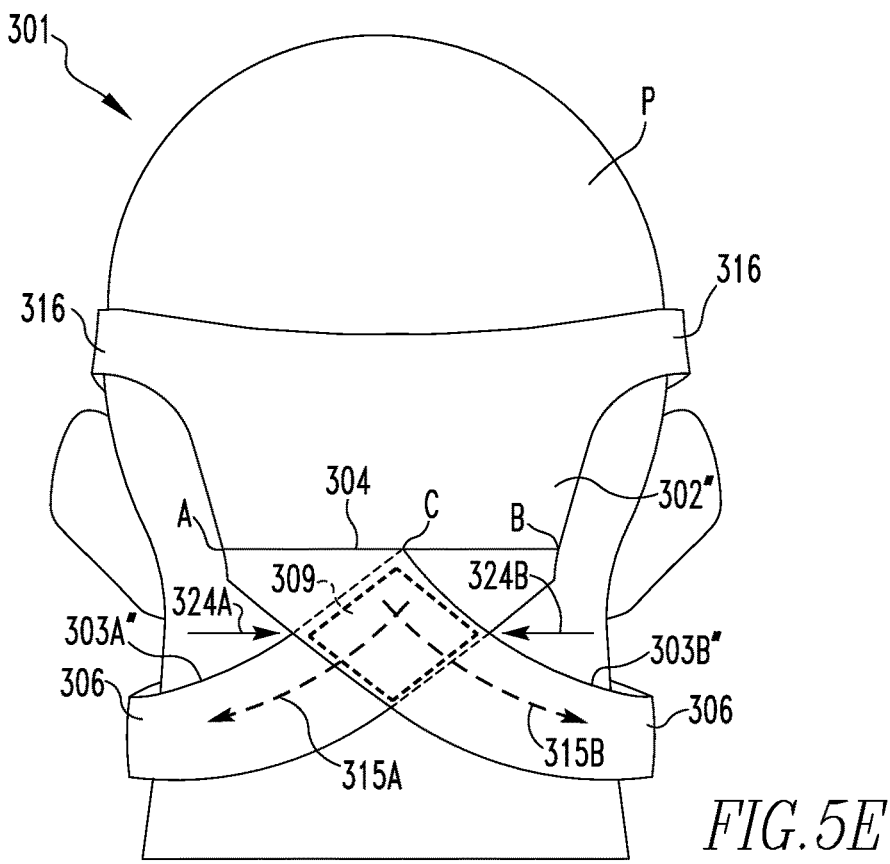
FIG. 5E shows yet another variation of the headgear shown in FIG. 5A in accordance with an exemplary embodiment of the present invention shown positioned on the head of a patient.

In a further non-limiting exemplary embodiment, referring to FIG. 5E, similar to the non-limiting exemplary embodiment shown in FIG. 5D, a wrapping panel 303A" can be produced by omitting material from the left side (with respect to the view shown in FIG. 5A) of wrapping panel 303A and a wrapping panel 303B" can be produced by omitting material from the right side (with respect to the view shown in FIG. 5A) of wrapping panel 303B, however, a greater quantity of material is omitted from the left side of wrapping panel 303A and from the right side of wrapping panel 303B in the embodiment shown in FIG. 5E than in the embodiment shown in FIG. 5D. Specifically, a top edge (with respect to the view shown in FIG. 5E) of wrapping panel 303A" only extends from a point B to a point C of seam 304 rather than extending from point B to a point A of seam 304, and a top edge (with respect to the view shown in FIG. 5E) of wrapping panel 303B" only extends from a point A to a point C of seam 304 rather than extending from point A to point B of seam 304, resulting in the overlap region 309 of the embodiment shown in FIG. 5E having a lesser area than the overlap region 309 of the embodiment shown in FIG. 5D.

Figure 5F:
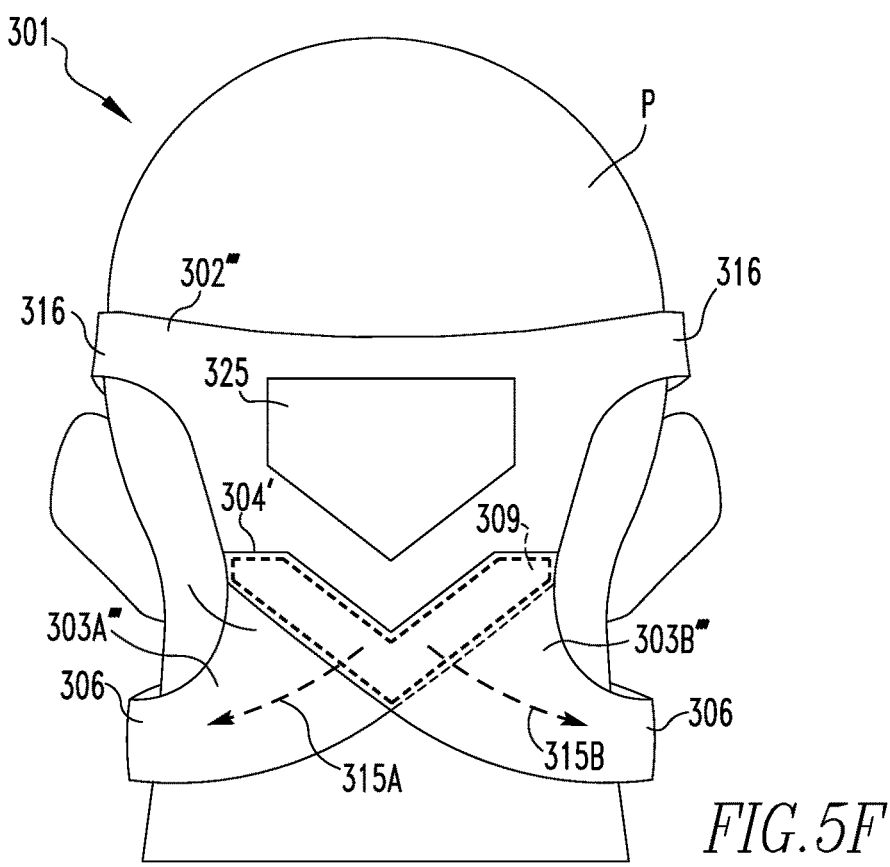
FIG. 5F shows still another variation of the headgear shown in FIG. 5A in accordance with an exemplary embodiment of the present invention shown positioned on the head of a patient.

In yet another non-limiting exemplary embodiment, referring to FIG. 5F, a horizontal panel 302'" can be produced by producing a bottom edge (with respect to the view shown in FIG. 5F) that extends down beyond the bottom edge (with respect to the view shown in FIG. 5A) of horizontal panel 302" in order to accommodate a vent 325 that is produced by creating an opening in horizontal panel 302'". To accommodate the bottom edge of horizontal panel 302'", wrapping panels 303A'" and 303B'" are produced with a top edge (with respect to the view shown in FIG. 5F) that aligns with the bottom edge of horizontal panel 302'", resulting in a non-linear seam 304'. For economy of disclosure, the various venting portions shown in FIGS. 5C-5F, as well as FIGS. 4C-4D, are only described with respect to headgear 301, however, it will be appreciated that such venting portions can also be adapted for incorporation in headgear 101 and 201 without departing from the scope of the disclosed concept.

While exemplary embodiments of the disclosed concept are shown coupled to particular patient interfaces and auxiliary components such as straps, masks, and tubing assemblies, it will be appreciated that the pairings of headgear and patient interfaces shown in the figures are illustrative and not meant to limit what type of patient interfaces and auxiliary components can be compatible with particular embodiments of the disclosed concept. In one non-limiting example, headgear 101 and headgear 202 are shown in FIGS. 2C and 3C as being coupled to patient interfaces that cover both the mouth and nose of patient P, but both headgear 101 and headgear 202 can easily be adapted for use with a patient interface that only covers the nose of patient P, such as patient interface 5. In another non-limiting example, headgear 101 can easily be adapted for coupling to the patient interface 205 and the number of tubing members 211 shown in FIG. 3C, and headgear 201 can easily be adapted for coupling to the patient interface 105 and lower strap portions 106 shown in FIG. 2C. In a further non-limiting example, headgear 301 can easily be adapted for coupling to the patient interface 205 and the number of tubing members 211 shown in FIG. 3C.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A headgear for use with a patient interface for supplying a pressurized flow of breathable gas to an airway of a patient and configured to secure the patient interface to a face of the patient, the headgear comprising:
    a first wrapping panel configured to be disposed against a rear side of a head of the patient, the first wrapping panel having an upper portion structured to be coupled to the patient interface via at least one upper strap portion and a lower portion structured to be coupled to the patient interface via a first lower strap portion passing below an ear of the patient along a first side of the head of the patient when the patient interface is secured to the face of the patient via the headgear; and
    a second wrapping panel configured to be disposed against a rear side of the head of the patient, the second wrapping panel having an uppermost edge directly coupled to an uppermost edge of the first wrapping panel, an upper portion of the second wrapping panel being structured to be coupled to the patient interface via the at least one upper strap portion, and a lower portion structured to be coupled to the patient interface via a second lower strap portion passing below another ear of the patient along a second side of the head of the patient opposite the first side,
    wherein a portion of the second wrapping panel overlaps a corresponding portion of the first wrapping panel in an overlap region disposed between the upper and lower portions of each of the first wrapping panel and the second wrapping panel, and
    wherein the upper portion of the first wrapping panel and the upper portion of the second wrapping panel are coupled via a first seam disposed at a first edge of the overlap region and a second seam disposed at a second edge of the overlap region opposite the first edge and spaced a distance from the first seam.

2. The headgear of claim 1, wherein the first wrapping panel and the second wrapping panel are coupled together solely at the upper portions thereof.

3. The headgear of claim 1 further comprising a stabilizing panel produced from an extensible material, the stabilizing panel being coupled to the lower portion of the first wrapping panel and the lower portion of the second wrapping panel.

4. A headgear for use with a patient interface for supplying a pressurized flow of breathable gas to an airway of a patient, wherein the headgear is configured to secure the patient interface to a face of the patient, the headgear comprising:
    a horizontal panel configured to be disposed against a rear side of a head of the patient, the horizontal panel having a first strap portion structured to be coupled to the patient interface and passing along a first side of the head of the patient when the patient interface is secured to the face of the patient via the headgear and having a second strap portion structured to be coupled to the patient interface and passing along a second side of the head of the patient opposite the first side when the patient interface is secured to the face of the patient via the headgear;
    a first wrapping panel configured to be disposed against the rear side of the head of the patient, the first wrapping panel having an upper portion coupled to the horizontal panel and a lower portion structured to be coupled to the patient interface via a first lower strap portion passing below an ear of the patient along the first side of the head of the patient when the patient interface is secured to the face of the patient via the headgear; and
    a second wrapping panel configured to be disposed against the rear side of the head of the patient, the second wrapping panel having an upper portion coupled to the horizontal panel at a common location as the first wrapping panel, the upper portion of the second wrapping panel being structured to be coupled to the patient interface and having a lower portion structured to be coupled to the patient interface via a second lower strap portion passing below an ear of the patient along the second side of the head of the patient when the patient interface is secured to the face of the patient via the headgear, wherein a portion of the second wrapping panel overlaps a corresponding portion of the first wrapping panel in an overlap region disposed between the upper and lower portions of each of the first wrapping panel and the second wrapping panel.

5. The headgear of claim 4, wherein the first wrapping panel and the second wrapping panel are coupled together solely at the upper portions thereof.

6. The headgear of claim 4, further comprising a stabilizing panel produced from an extensible material, the stabilizing panel being coupled to the lower portion of the first wrapping panel and the lower portion of the second wrapping panel.

7. The headgear of claim 4, wherein a thickness of the portion of the first wrapping panel in the overlap region is less than a thickness of portions of the first wrapping panel not in the overlap region, and wherein a thickness of the portion of the second wrapping panel in the overlap region is less than a thickness of portions of the second wrapping panel not in the overlap region.

8. The headgear of claim 4, further comprising a number of venting portions, each of the number of venting portions comprising at least one of: a number of openings in the portion of the first wrapping panel in the overlap region, a number of openings in the portion of the second wrapping panel in the overlap region, and/or a number of openings in the horizontal panel.

9. An arrangement for providing a flow of breathing gas to an airway of a patient, the arrangement comprising:
 a patient interface structured to be operatively coupled to a breathing gas generator via a delivery conduit; and
 a headgear configured to secure the patient interface to a face of the patient, the headgear comprising:
  a first wrapping panel configured to be disposed against a rear side of a head of the patient, the first wrapping panel having an upper portion structured to be coupled to the patient interface and a lower portion structured to be coupled to the patient interface via a first lower strap portion passing below an ear of the patient along a first side of the head of the patient when the patient interface is secured to the face of the patient via the headgear; and
  a second wrapping panel configured to be disposed against the rear side of the head of the patient, the second wrapping panel having an uppermost edge directly coupled to an uppermost edge of the first wrapping panel, an upper portion of the second wrapping panel being structured to be coupled to the patient interface, and a lower portion structured to be coupled to the patient interface via a second lower strap portion passing below an ear of the patient along a second side of the head of the patient opposite the first side when the patient interface is secured to the face of the patient via the headgear, wherein a portion of the second wrapping panel overlaps a corresponding portion of the first wrapping panel in an overlap region disposed between the upper and lower portions of each of the first wrapping panel and the second wrapping panel.

10. The arrangement of claim 9, wherein the upper portion of the first wrapping panel is coupled to the patient interface via at least one first upper strap portion, and wherein the upper portion of the second wrapping panel is coupled to the patient interface via at least one second upper strap portion.

11. The arrangement of claim 10, further comprising:
 a manifold structured to be operatively coupled to the delivery conduit; and
 a number of tubing members, each tubing member having a first end operatively coupled to the manifold and a second end operatively coupled to the patient interface (205).

12. The arrangement of claim 11,
 wherein the at least one first upper strap portion of the first wrapping panel is coupled to the patient interface via a first tubing member of the number of tubing members, and
 wherein the at least one second upper strap portion of the second wrapping panel is coupled to the patient interface via a second tubing member of the number of tubing members.

13. The arrangement of claim 11, further comprising:
 a horizontal panel configured to be disposed against the rear side of the head of the patient, the horizontal panel having a first strap portion structured to be coupled to the patient interface and passing along the first side of the head of the patient when the patient interface is secured to the face of the patient via the headgear and a second strap portion structured to be coupled to the patient interface and passing along the second side of the head of the patient when the patient interface is secured to the face of the patient via the headgear,
 wherein the upper portion of the first wrapping panel is coupled to the horizontal panel and is structured to be coupled to the patient interface via the horizontal panel, and
 wherein the upper portion of the second wrapping panel is coupled to the horizontal panel and is structured to be coupled to the patient interface via the horizontal panel.

14. The arrangement of claim 13, further comprising a number of venting portions, wherein the number of venting portions comprises at least one of: a number of openings in the portion of the first wrapping panel in the overlap region, a number of openings in the portion of the second wrapping panel in the overlap region, and/or a number of openings in the horizontal panel.

\* \* \* \* \*